United States Patent [19]

Cole-Hamilton et al.

[11] Patent Number: 5,442,112
[45] Date of Patent: Aug. 15, 1995

[54] PREPARATION OF DIALKYL TELLURIUM AND DIALKYL SELENIUM

[75] Inventors: David J. Cole-Hamilton, Fife, United Kingdom; Ewan McQueen, Sydney, Australia

[73] Assignee: The Secretary of State for Defence in Her Britannic Majesty's Government of the United Kingdom of Great Britain and Northern Ireland, Hants, United Kingdom

[21] Appl. No.: 211,402

[22] PCT Filed: Sep. 29, 1992

[86] PCT No.: PCT/GB92/01782
§ 371 Date: Jun. 13, 1994
§ 102(e) Date: Jun. 13, 1994

[87] PCT Pub. No.: WO93/07117
PCT Pub. Date: Apr. 15, 1993

[30] Foreign Application Priority Data

Oct. 3, 1991 [GB] United Kingdom ............... 9121000

[51] Int. Cl.$^6$ ............... C07F 11/00; C07C 395/00; C07C 391/00
[52] U.S. Cl. .................................................. 562/899
[58] Field of Search ....................................... 562/899

[56] References Cited

U.S. PATENT DOCUMENTS

| | | | |
|---|---|---|---|
| 5,043,476 | 8/1991 | Higa et al. | 562/899 |
| 5,075,500 | 12/1991 | Higa et al. | 562/899 |
| 5,091,570 | 2/1992 | Mullin et al. | 562/899 |
| 5,166,428 | 11/1992 | Cole-Hamilton et al. | 562/899 |
| 5,312,983 | 5/1994 | Brown et al. | 562/899 |

Primary Examiner—Paul F. Shaver
Attorney, Agent, or Firm—Nixon & Vanderhye

[57] ABSTRACT

Dialkyl SE and TE compounds are prepared by reacting a Na chalcogenide with a alkyl halide in a two-phase system of solvents.

12 Claims, 1 Drawing Sheet

PREPARATION OF DIALKYL TELLURIUM AND DIALKYL SELENIUM

This application is a 35USC371 of PCT/GR92/01782, filed Sep. 29, 1992.

This invention relates to a method for the preparation of dialkyls of the group VI metals tellurium and selenium.

The metals tellurium and selenium are of importance in semiconductor technology, for example, in the preparation of the infrared detector material cadmium mercury telluride (CMT) and in light sensing switches respectively.

Frequently, these metals or, in particular, their compounds such as CMT are deposited on substrates by the process of Metal-Organic Vapour Phase Epitaxy (MOVPE) which involves vapour phase co-decomposition of volatile compounds of the component metals, in the case of tellurium this is most usually a dialkyl. Dialkyls have the advantages that as well as being volatile they can be easily purified by formation of adducts which can be easily decomposed to form the pure dialkyl as described for example in GB-A-850955 and PCT/GB88/01062. Dialkyl ditellurides, in addition to being useful as precursors in MOVPE, may also be used to prepare unsymmetrical dialkyls (for example in GB 8913799.6).

Unsymmetrical dialkyls are thought to be advantageous for MOVPE because they have the potential for combining high volatility with low temperatures for deposition of the desired material.

The literature preparation of $Me_2Te_2$ involves the use of large quantities of liquid ammonia and sodium metal (M. T. Chen and J. W. George *J. Organometallic Chemistry*, 1968, 12, p40), 1973). Apart from the dangerous nature of this reaction, the yields are extremely variable (from 15–60%).

Other methods using more convenient aqueous routes (D. V. Shenai-Khatkhate, E. D. Orrell, J. B. Mullin, D. C. Cupertino and D. J. Cole-Hamilton, *J. Crystal Growth* 77 (1986), 27 and K. J. Irgolic, *Methods of Organic Chemistry* (Houben-Weyl) vol E 12b Ed D Klamann Verlag Stuttgart 1990 and references therein) involving reaction of $Na_2Te_2$ or $Na_2Te$ with methyliodide resulted in low yields, typically 5–15% for $Me_2Te_2$ and about 30% for $Me_2Te$.

There is therefore a need for an improved method of preparation of dialkyl tellurium, dialkyl selenium, dialkyl ditelluride and dialkyl diselenide, both as direct precursors for MOVPE, and particularly as precursors for unsymmetrical dialkyls in the case of dialkyl ditellurides and dialkyl diselenides.

According to the present invention there is provided a method of preparation of dialkyl tellurium, dialkyl selenium, dialkyl ditelluride and dialkyl diselenide characterised by the reaction of a sodium chalcogenide with an alkyl halide in a two-phase system of solvents, the said two-phase system comprising water and an organic solvent immiscible with water, and by the addition of a phase-transfer catalyst. The phase-transfer catalyst is preferably a quarternary ammonium salt; cetyltrimethylammonium bromide (CTAB) has been found to be most satisfactory.

The sodium chalcogenide may be $Na_2Te$, $Na_2Te_2$, $Na_2Se$ or $Na_2Se_2$.

The alkyl may be a primary or secondary alkyl containing 1–20 carbon atoms, preferably 1–4 carbon atoms.

The alkyl is most preferably methyl.

The two-phase system may comprise water and an organic solvent immiscible with water, for example diethyl ether, benzene, toluene and the like.

Preferably, the organic solvent is diethyl ether.

BRIEF DESCRIPTION OF DRAWING

The invention will be further apparent from the following description with reference to the single FIGURE, which shows, by way of example only, one form of the method embodying same.

The numbers in bold refer to the FIGURE.

EXAMPLE 1

Preparation of Dimethylditelluride ($Me_2Te_2$)

Figure 1:
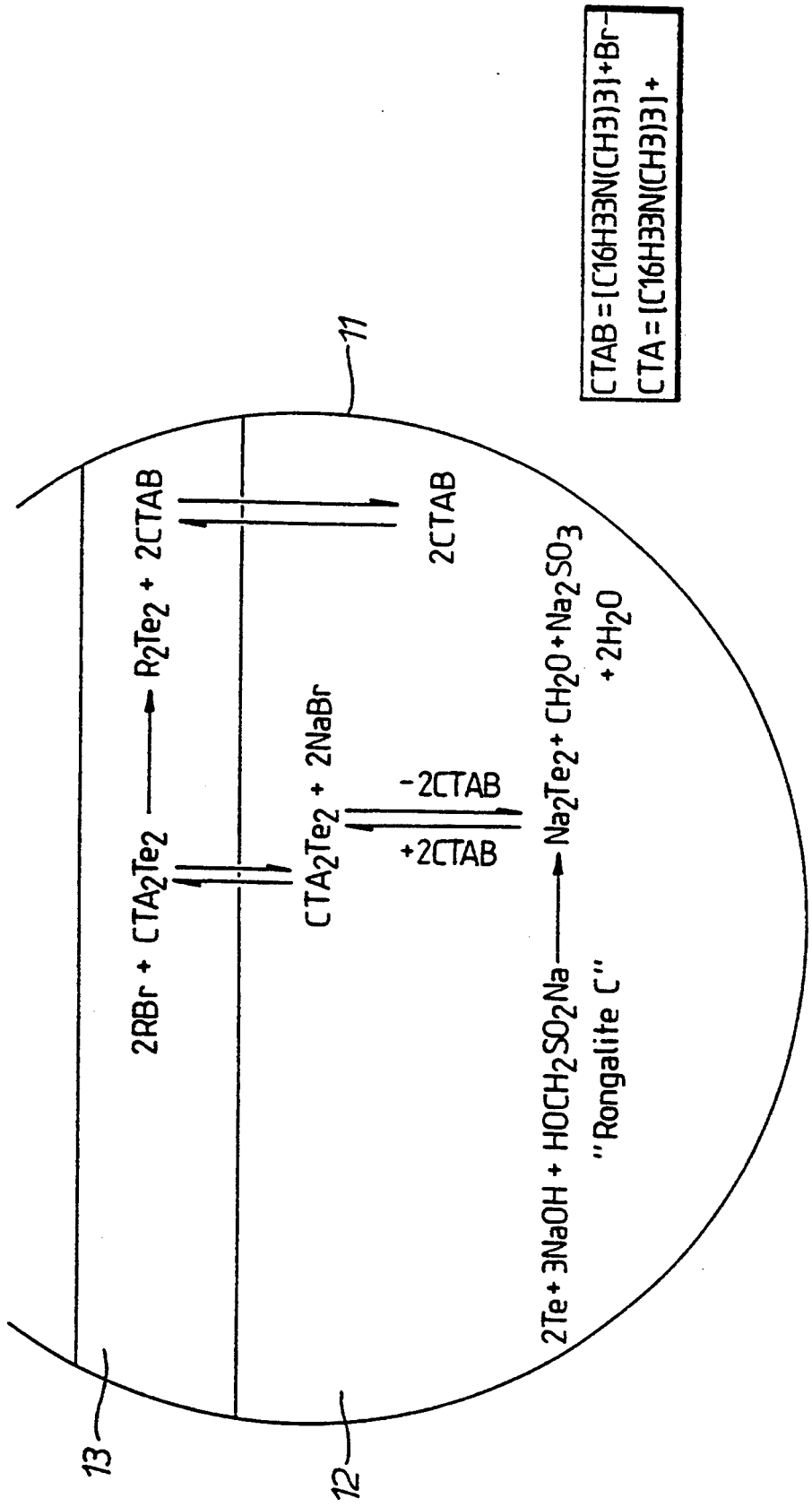

40.3 g (0.32 mol) of Te powder, 58.4 g (0.38 mol) sodium formaldehyde sulphoxylate (Rongalite C) and 50.0 g (1.25 mol) NaOH was dissolved in 300 cm³ of deaereated, distilled water in a flask 11 and the flask 11 heated to 110° C. in an oil bath for one hour and then cooled rapidly forming the aqueous layer 12. 0.75 g (2.0 mmol) CTAB in 500 cm³ of solvent ether was added followed by dropwise addition of 22 cm³ (0.35 mol) methyliodide forming the ethereal layer 13. The reaction mixture was stirred overnight at room temperature. The next morning, the flask 11 was heated to 40° C. for 2 hours and then left stirring at room temperature for 3 hours. The ether layer 13 was separated off and 250 cm³ solvent ether, 0.5 g CTAB and 5 cm³ methyliodide added to the aqueous layer 12. The flask 11 and contents were then warmed to 30° C. and stirred for ca. 2 hours.

The ether layers 13 were combined and the aqueous layer 12 again extracted with diethylether containing 5 cm³ methyliodide and 0.5 g CTAB. The ether layers 13 were orange-black in colour and dried using $CaCl_2$ and $CaH_2$. Removal of the ether gave ca. 35 g of a red-black oil. Dimethyltellurium (8.0 g, 16%) was removed by vacuum distillation to leave pure dimethylditelluride (25.5 g, 57%).

Since the alkyl halide e.g. methyliodide is more soluble in the organic phase, reaction with the water soluble $Na_2Te_2$ may be inhibited. For this reason the phase transfer catalyst CTAB is employed. This reagent allows transfer of the $Te_2^{2-}$ ion into the organic layer 13 where it may then react with the alkylhalide to produce $Me_2Te_2$.

The $Me_2Te_2$ thus produced in the organic layer 13 will be protected from breakdown (being lipophilic) and thus this process results in high yield.

EXAMPLE 2

Preparation of Dimethyltellurium ($Me_2Te$)

150 g (3.75 mol) NaOH, 174 g (1.13 mol) Rongalite C and 57.3 g (0.45 mol) tellurium powder were added to 1,000 cm³ of deaereated, distilled water in a flask 11 and the reaction mixture heated to 100° C. for ca. 2 hours. The temperature was then raised to 120° C. and the flask 11 then cooled to room temperature. A solution of 1.0 g (2.8 mol) CTAB in 250 cm³ diethyl ether was added to give a two-phase system (FIG. 1). 56.4 cm³ (0.91 mol) methyliodide was added, initially dropwise and then in a steady stream. The lower aqueous layer 12 was heated to 40° C. for 30 minutes and then the flask contents were stirred at room temperature overnight.

The next morning the flask contained a clear, clean, aqueous layer 12 and a pale-yellow ethereal layer 13 with no sign of tellurium metal.

The ether layer 13 was separated off. The aqueous layer 12 was extracted with 2×200 cm³ portions of ether and the ether extracts combined and dried over $CaCl_2$ and $CaH_2$. The ether was removed by distillation to give a yellow oil. Purification by distillation at reduced pressure gave 47.0 g (0.30 mol) dimethyltellurium. Yield=66%. Only a trace of dimethylditelluride was observed during work-up.

To determine the effect of the ether layer and the CTAB, the reaction was repeated:

(i) using ether, but no CTAB. After overnight, stirring the aqueous layer 12 was purple in colour and a white solid had formed at the junction between the layers. The ether layer 13 was pale yellow. Work-up of the product gave a yield of dimethyltellurium of 47%, and (ii) with no ether and no CTAB. After heating and overnight stirring, the flask contained a pale yellow aqueous layer 12, a dark grey precipitate (presumably tellurium metal) and pools of dimethyltellurium on the surface of the water. Extraction with ether gave an orange solution. Isolation of the product by distilling off the ether gave 30% of dimethyltellurium which was contaminated with dimethylditelluride.

These results indicate the importance of both the two phase system and the need for CTAB to act as a phase transfer agent.

The two-phase system may be used to prepare other organo-tellurium and organo-selenium precursors.

We claim:

1. A method of preparing dialkyl tellurium, dialkyl selenium, dialkyl ditelluride and dialkyl diselenide, said method comprising the steps of
   (a) reacting a sodium chalcogenide with an alkyl halide in a two-phase system of solvents and by the addition of a phase-transfer catalyst, said two phase system comprising water and an organic solvent immiscible with water, and thereafter
   (b) separating the reaction product.

2. The method according to claim 1, in which the phase-transfer catalyst is a quaternary ammonium salt.

3. The method according to claim 2, in which the phase-transfer catalyst is cetyltrimethylammonium bromide.

4. The method according to claim 1, in which the sodium chalcogenide is $Na_2Te$.

5. The method according to claim 1, in which the sodium chalcogenide is $Na_2Te_2$.

6. The method according to claim 1, in which the sodium chalcogenide is $Na_2Se$.

7. The method according to claim 1, in which the sodium chalcogenide is $NaSe_2$.

8. The method according to claim 1, in which the alkyl in the alkyl halide is a primary or secondary alkyl containing 1–20 carbon atoms.

9. The method according to claim 8 which the alkyl is methyl.

10. The method according to claim 1, in which the organic solvent is diethyl ether.

11. The method according to claim 1, in which the organic solvent is benzene.

12. The method according to claim 1, in which the organic solvent is toluene.

* * * * *